United States Patent [19]

Mayer et al.

[11] 4,020,063
[45] Apr. 26, 1977

[54] OXADIAZEPINE CATIONIC DYESTUFFS

[75] Inventors: Uwe Mayer, Cologne; Karl-Heinz Schundehutte, Opladen, both of Germany

[73] Assignee: Bayer Aktiengesellschaft, Leverkusen, Germany

[22] Filed: Aug. 24, 1973

[21] Appl. No.: 391,298

[30] Foreign Application Priority Data

Aug. 24, 1972 Germany .................... 2241626

[52] U.S. Cl. .............. 260/247.5 H; 260/239 DD; 260/239.3 T; 260/242; 260/293.58; 260/294.8 B; 260/295 T; 260/296 H; 260/326.13 R; 260/327 B; 260/333; 260/347.3

[51] Int. Cl.$^2$ .................... C07D 273/06

[58] Field of Search ............ 260/239 DD, 247.5 H, 260/165, 333, 293.58

[56] References Cited

UNITED STATES PATENTS 3,133,086  5/1964  Bossard et al. ............... 260/333
3,840,518  10/1974  Schmitt et al. ............... 260/165

Primary Examiner—Lorraine A. Weinberger
Assistant Examiner—Michael Shippen
Attorney, Agent, or Firm—Plumley and Tyner

[57] ABSTRACT

Cationic dyestuffs of the formula

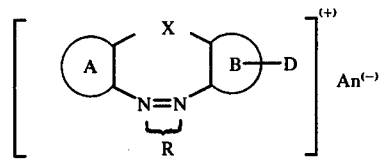

wherein
A and B denote aromatic-carbocyclic or aromatic-heterocyclic radicals,
D denotes the groups —O—$R_2$,

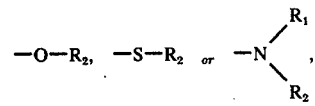

R denotes hydrogen, alkyl, aralkyl, alkenyl, alkoxy or aryl,
X denotes a bridge member and
$An^{(-)}$ denotes an anion,
are suitable for dyeing and printing of natural and synthetic materials, particularly of polyacrylonitrile, copolymers of acrylonitrile with other vinyl compounds, of acid modified polyesters and acid modified polyamides.

7 Claims, No Drawings

OXADIAZEPINE CATIONIC DYESTUFFS

The invention relates to cationic dyestuffs of the general formula

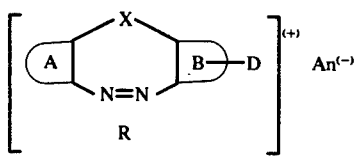    I wherein
A and B denote aromatic-carbocyclic or aromatic-heterocyclic radicals to which further rings can be fused,
D denotes the groups $-O-R_2$,

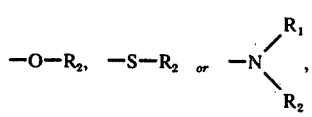

$R_1$ denotes hydrogen, alkyl, aralkyl, alkenyl or aryl,
$R_2$ denotes hydrogen, alkyl, aralkyl, aryl, a heterocyclic radical or a $-NH_2$ group or a group of the general formula

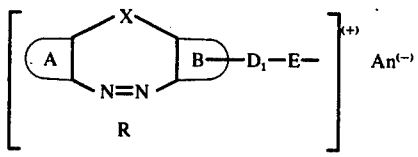    II the radicals $R_1$ and $R_2$ can be cyclised with one another or with B,
E denotes a direct bond or a bridge member,
$D_1$ denotes the groups $-O-$, $-S-$ or $-N(R_1)-$,
R denotes hydrogen, alkyl, aralkyl, alkenyl, alkoxy or aryl,
X denotes a bridge member and
$An^{(-)}$ denotes an anion
and wherein
the rings A and B and the cyclic and acyclic radicals can carry further non-ionic substituents.

Within the framework of the general formula I, the invention thus relates to dyestuffs of the formulae

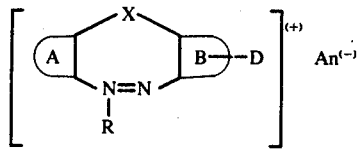    III and

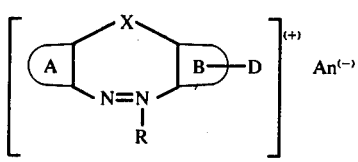    IV wherein

A, B, X, D, R and $An^{(-)}$ have the indicated meaning and in the case of the formula (III), the radical R in the radical (II) is on the left-hand N and in the case of the formula (IV) the radical R in the formula (II) is on the righthand N atom.

The formula is to be understood as meaning that the invention is concerned with dyestuffs of type III and type IV. The products can be either mixtures of types III and IV or the pure individual dyestuffs.

Furthermore, the present invention relates to the manufacture of the dyestuffs and their use for dyeing and printing natural and synthetic materials.

Amongst the dyestuffs of the general formulae I or III and IV, dyestuffs to be singled out are those in which the bridge member X is a constituent of a 7-membered or 8-membered ring and represents, for example, the following groups: $-O-$, $-S-$, $-SO_2-$, $-SO_2-O-$,

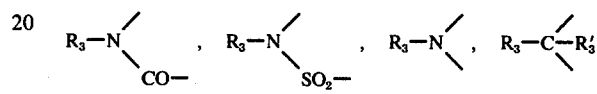

or $-CR_3''-$.
Herein
$R_3$ and $R_3'$ denote hydrogen, alkyl, aralkyl, alkenyl or aryl and
$R_3''$ denotes oxygen, sulphur or N-Y, and Y=alkyl or aryl. The alkyl and aryl radicals can carry non-ionic substituents and the alkyl radicals can be cyclised to form the rings A or B.

Suitable bridge members E are, in particular, the following:

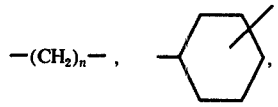

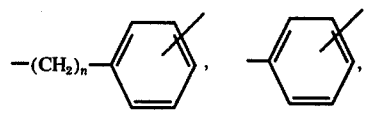

wherein
n represents a number from 1 to 4 and
the aromatic radicals can possess further substituents, or the radicals $-S-$alkylene$-$, $-O-$alkylene$-$,

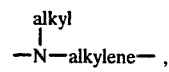

$-NHCO-$alkylene, $-CONH-$alkylene$-$, $-NHSO_2-$alkylene$-$, $-SO_2-NH-$alkylene,

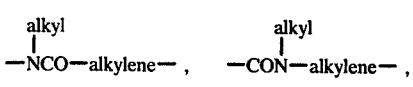

$-CO-$alkylene$-$, $-COO-$alkylene$-$, $-$alkylene$-O-$alkylene$-$, $-$alkylene$-S-$alkylene$-$, $-$alkylene$-NHCO-$alkylene$-$, $-$alkylene$-CONH-$alkylene$-$, $-$alkylene$-SO_2NH-$alkylene$-$, —alkylene—NHSO₂—alkylene— or —alkylene—OCO—alkylene—
wherein alkyl and alkylene represents groups with 1 – 4 C atoms which can be substituted.

Non-ionic substitutents in the sense of the present invention are the non-dissociating substituents which are customary in dyestuff chemistry, such as halogen, alkyl, aralkyl, alkenyl, aryl, hydroxyl, alkoxy, aralkoxy, aryloxy, alkylthio, aralkylthio, arylthio, nitro, nitrile, alkoxycarbonyl, formyl, alkylcarbonyl, arylcarbonyl, aralkylcarbonyl, alkoxycarbonyloxy, alkylcarbonylamino, arylcarbonylamino, alkylsulphonylamino, arylsulphonylamino, ureido, N-aryl- or N-alkyl-ureido, aryloxycarbonylamino, alkoxycarbonylamino, carbamoyl, N-alkylcarbamoyl, N,N-dialkylcarbamoyl, N-alkyl-N-aryl-carbamoyl, sulphamoyl, N-alkylsulphamoyl, N,N-dialkylsulphamoyl, carboxylic acid alkyl ester, carboxylic acid aryl ester, sulphonic acid alkyl ester or sulphonic acid aryl ester groups, with the alkyl radicals mentioned preferably containing 1 – 4 C atoms and the aryl groups preferably belonging to the phenyl or naphthalene series, and also radicals of the heterocyclic series such as thienyl, thenoyl, furyl, furoyl, pyrryl, pyrroyl, pyridyl or pyridoyl.

Suitable rings A are, for example, the pyridine ring and especially the benzene ring.

Suitable rings B are, for example, the benzene ring or the naphthalene ring.

Examples of suitable non-ionic substituents of the ring A are: fluorine, chlorine, bromine, methyl, ethyl, n-propyl, isopropyl, n-butyl, isobutyl, tert.-butyl, iso-amyl, cyclohexyl, β-chloroethyl, β-cyanoethyl, β-hydroxyethyl, β- or γ-hydroxypropyl, benzyl, phenyl, hydroxyl, methoxy, ·ethoxy, n-propoxy, iso-propoxy, n-butoxy, β-methoxyethoxy, β-ethoxyethoxy, benzyloxy, 2-phenylethyloxy, phenylpropyl-(2,2)-oxy, phenoxy, $C_1$ to $C_3$-alkylthio, benzylthio, phenylthio, nitro, nitrile, methoxycarbonyl, ethoxycarbonyl, n-butoxycarbonyl, phenoxycarbonyl, phenyloxysulphonyl, formyl, acetyl, n-propionyl, n-butyryl, benzoyl, benzylcarbonyl, acetylamino, benzoylamino, methylsulphonylamino, ethylsulphonylamino, phenylsulphonylamino, ureido, N-phenylureido, N-methylureido, carbamoyl, N-methylcarbamoyl, N,N-dimethylcarbamoyl, N-methyl-N-phenylcarbamoyl, sulphamoyl, N-methylsulphamoyl, N-ethylsulphamoyl, N,N-dimethylsulphamoyl, N,N-diethylsulphamoyl, methylsulphonyl, ethylsulphonyl, N-propylsulphonyl, N-butylsulphonyl, benzylsulphonyl, phenylsulphonyl, methoxycarbonylmethyl and ethoxycarbonylmethyl, it being possible for the phenyl radicals to be substituted by methyl, halogen, nitrile or nitro, and also amino radicals wherein substituents which can be present are hydrogen, methyl, ethyl or propyl, which can be substituted by chlorine, bromine, nitrile, thiocyanato, hydroxyl, methoxy, ethoxy, chloroethoxy, bromoethoxy, cyanoethoxy, acetoxy, propionyloxy, butyryloxy, benzoyloxy, methoxycarbonyl, ethoxycarbonyl, phenoxycarbonyl, methoxycarbonyloxy, ethoxycarbonyloxy or phenoxycarbonyloxy, cyclohexyl, benzyl or phenyl, it being possible for the phenyl radical to be substituted by alkyl with 1 to 2 C atoms, halogen, nitrile or nitro; the substituents of the amino radicals can also be bonded to one another to form a 5-membered or 6-membered ring.

Examples of suitable non-ionic substituents of the ring B are: chlorine, bromine, $C_1$ to $C_5$-alkyl, β-chloroethyl, β-cyanoethyl, β-hydroxyethyl, cyclohexyl, benzyl, hydroxyl, $C_1$ to $C_4$-alkoxy, β-methoxyethoxy, β-ethoxyethoxy, benzyloxy, 2-phenylethyloxy, phenylpropyl-(2,2)-oxy, phenoxy, $C_1$ to $C_3$-alkylthio, benzylthio or phenylthio.

By an alkyl or alkenyl radical there is understood a saturated or unsaturated radical with 1 to 6 or 3 to 6 C atoms, such as methyl, trifluoromethyl, ethyl, β-chloroethyl, β-bromoethyl, β-hydroxyethyl, β-methoxyethyl, β-cyanoethyl, β-acetoxyethyl, β-aminocarbonylethyl, i-propyl, n-butyl, i-butyl, t-butyl or i-amyl or allyl, methallyl, γ-chloroallyl or propargyl.

Examples of possible aralkyl radicals are: phenylmethyl, phenylethyl, phenylpropyl-(2,2) and optionally their derivatives substituted by chlorine, methyl or methoxy in the phenyl nucleus.

As cycloalkyl, cyclohexyl is of particular importance.

Aryl preferably represents phenyl and naphthyl and their derivatives such as 4-methylphenyl, 2-methylphenyl, 4-chlorophenyl, 2-chlorophenyl and 2-methyl-4-chlorophenyl.

Possible anionic radicals An⁻ are the organic and inorganic anions which are customary for cationic dyestuffs.

Examples of inorganic anions are fluoride, chloride, bromide and iodide, perchlorate, hydroxyl, radicals of acids containing S, such as bisulphate, sulphate, disulphate and aminosulphate; radicals of nitrogen-oxygen acids, such as nitrate; radicals of oxygen acids of phosphorus, such as dihydrogen phosphate, hydrogen phosphate, phosphate and metaphosphate; radicals of carbonic acid, such as bicarbonate and carbonate; further anions of oxygen acids and complex acids, such as methosulphate, ethosulphate, hexafluosilicate, cyanate, thiocyanate, ferrocyanide, ferricyanide, trichlorozincate and tetrachlorozincate, tribromozincate and tetrabromozincate, stannate, borate, divanadate, tetravanadate, molybdate, tungstate, chromate, bichromate and tetrafluoborate, as well as anions of esters of boric acid, such as of the glycerine ester of boric acid, and of esters of phosphoric acid, such as of methylphosphate.

Examples of organic anions are anions of saturated or unsaturated aliphatic, cycloaliphatic, aromatic and heterocyclic carboxylic acids and sulphonic acids, such as radicals of acetic acid, chloroacetic acid, cyanoacetic acid, hydroxyacetic acid, aminoacetic acid, methylaminoacetic acid, aminoethylsulphonic acid, methylaminoethylsulphonic acid, propionic acid, n-butyric acid, i-butyric acid, 2-methyl-butyric acid, 2-ethyl-butyric acid, dichloroacetic acid, trichloroacetic acid, trifluoroacetic acid, 2-chloropropionic acid, 3-chloropropionic acid, 2-chlorobutyric acid, 2-hydroxypropionic acid, 3-hydroxypropionic acid, O-ethylglycollic acid, thioglycollic acid, glyceric acid, malic acid, dodecyl-tetraethylene glycolether-propionic acid, 3-(nonyloxy)-propionic acid, 3-(isotridecyloxy)-propionic acid, 3-(isotridecyloxy)-diethylene glycoletherpropionic acid, the ether-propionic acid of the alcohol mixture with 6 to 10 carbon atoms, thioacetic acid, 6-benzoylamino-2-chlorocaproic acid, nonylphenol-tetraethylene glycolether-propionic acid, nonylphenol-diethylene glycol-etherpropionic acid, dodecyl-tetraethylene glycol-ether propionic acid, phenoxyacetic acid, nonylphenoxyacetic acid, n-valeric acid, i-valeric acid, 2,2,2-trimethylacetic acid, n-caproic acid, 2-ethyl-n-caproic acid, stearic acid, oleic acid, ricinoleic acid, palmitic acid, n-pelargonic acid, lauric acid, a mixture of aliphatic carboxylic acids with 9 to 11 carbon atoms (Versatic Acid 911 from SHELL), a mixture of aliphatic carboxylic acids with 15 to 19 carbon atoms (Versatic Acid 1519 from SHELL), coconut fatty acid first runnings, undecanecarboxylic acid, n-tridecanecarboxylic acid and a coconut fatty acid mixture; acrylic acid, methacrylic acid, crotonic acid, propargylic acid, oxalic acid, malonic acid, succinic acid, glutaric acid, adipic acid, pimelic acid, suberic acid, azelaic acid, the isomer mixture of 2,2,4- and 2,4,4-trimethyladipic acid, sebacic acid, isosebacic acid (isomer mixture), tartaric acid, citric acid glyoxylic acid, dimethyl ether-α,α'-dicarboxylic acid, methylene-bis-thioglycollic acid, dimethyl sulphide-α,α-dicarboxylic acid, 2,2'-dithio-di-n-propionic acid, fumaric acid, maleic acid, itaconic acid, ethylene-bisiminoacetic acid, nitrilosulphonic acid, methanesulphonic acid, ethanesulphonic acid, chloromethanesulphonic acid, 2-chloroethanesulphonic acid and 2-hydroxyethanesulphonic acid and Mersolat, that is to say $C_8$–$C_{15}$ paraffinsulphonic acid, obtained by chlorosulphonation of paraffin oil.

Examples of suitable anions of cycloaliphatic carboxylic acids are the anions of cyclohexanecarboxylic acid and cyclohexene-3-carboxylic acid and examples of anions of araliphatic monocarboxylic acids are anions of phenylacetic acid, 4-methylphenylacetic acid and mandelic acid.

Suitable anions of aromatic carboxylic acids are, for example, the anions of benzoic acid, 2-methylbenzoic acid, 3-methylbenzoic acid, 4-methylbenzoic acid, 4-tert.-butylbenzoic acid, 2-bromobenzoic acid, 2-chlorobenzoic acid, 3-chlorobenzoic acid, 4-chlorobenzoic acid, 2,4-dichlorobenzoic acid, 2,5-dichlorobenzoic acid, 2-nitrobenzoic acid, 3-nitrobenzoic acid, 4-nitrobenzoic acid, 2-chloro-4-nitrobenzoic acid, 6-chloro-3-nitro-benzoic acid, 2,4-dinitrobenzoic acid, 3,4-dinitrobenzoic acid, 3,5-dinitrobenzoic acid, 2-hydroxybenzoic acid, 3-hydroxybenzoic acid, 4-hydroxybenzoic acid, 2-mercaptobenzoic acid, 4-nitro-3-methylbenzoic acid, 4-aminobenzoic acid, 5-nitro-2-hydroxybenzoic acid, 3-nitro-2-hydroxybenzoic acid, 4-methoxybenzoic acid, 3-nitro-4-methoxybenzoic acid, 4-chloro-3-hydroxybenzoic acid, 3-chloro-4-hydroxybenzoic acid, 5-chloro-2-hydroxy-3-methylbenzoic acid, 4-ethylmercapto-2-chlorobenzoic acid, 2-hydroxy-3-methylbenzoic acid, 6-hydroxy-3-methylbenzoic acid, 2-hydroxy-4-methylbenzoic acid, 6-hydroxy-2,4-dimethylbenzoic acid, 6-hydroxy-3-tert.-butylbenzoic acid, phthalic acid, tetrachlorophthalic acid, 4-hydroxyphthalic acid, 4-methoxyphthalic acid, isophthalic acid, 4-chloroisophthalic acid, 5-nitro-isophthalic acid, terephthalic acid, nitroterephthalic acid and diphenyl-3,4-carboxylic acid, o-vanillic acid, 3-sulphobenzoic acid, benzene-1,2,4,5-tetracarboxylic acid, naphthalene-1,4,5,8-tetracarboxylic acid, biphenyl-4-carboxylic acid, abietic acid, phthalic acid mono-n-butyl ester, terephthalic acid monomethyl ester, 3-hydroxy-5,6,7,8-tetrahydronaphthalene-2-carboxylic acid, 2-hydroxy-1-naphthoic acid and anthraquinone-2-carboxylic acid.

Examples of suitable anions of heterocyclic carboxylic acids are the anions of pyromucic acid, dehydromucic acid and indolyl-3-acetic acid.

Examples of suitable anions of aromatic sulphonic acids are the anions of benzenesulphonic acid, benzene-1,3-disulphonic acid, 4-chlorobenzenesulphonic acid, 3-nitrobenzenesulphonic acid, 6-chloro-3-nitro-benzenesulphonic acid, toluene-4-sulphonic acid, toluene-2-sulphonic acid, toluene-ω-sulphonic acid, 2-chlorotoluene-4-sulphonic acid, 2-hydroxybenzenesulphonic acid, n-dodecylbenzenesulphonic acid, 1,2,3,4-tetrahydronaphthalene-6-sulphonic acid, naphthalene-1-sulphonic acid, naphthalene-1,4- or -1,5-disulphonic acid, naphthalene-1,3,5-trisulphonic acid, 1-naphthol-2-sulphonic acid, 5-nitronaphthalene-2-sulphonic acid, 8-aminonaphthalene-1-sulphonic acid, stilbene-2,2'-disulphonic acid and biphenyl-2-sulphonic acid.

An example of a suitable anion of a heterocyclic sulphonic acid is the anion of quinoline-5-sulphonic acid.

Further anions which can be used are those of arylsulphinic, arylphosphonic and arylphosphonous acids, such as benzenesulphinic acid and benzenephosphonic acid.

Colourless anions are preferred. For dyeing from an aqueous medium, anions which do not excessively impair the solubility of the dyestuff in water are preferred. For dyeing from organic solvents, anions which assist the solubility of the dyestuff in organic solvents or at least do not influence it adversely are frequently also preferred.

The anion is in general decided by the manufacturing process and by the purification of the crude dyestuff which may be carried out. In general the dyestuffs are in the form of halides (especially chlorides or bromides) or methosulphates, ethosulphates, sulphates, benzenesulphonates or toluenesulphonates, or acetates. The anions can be replaced by other anions in a known manner.

Preferred dyestuffs of the formula (I) correspond to the formula

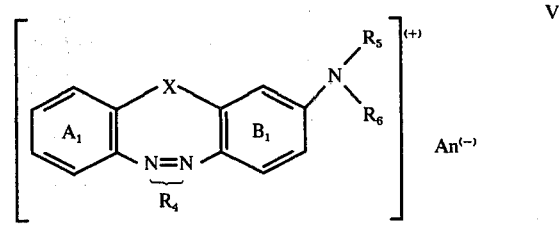

V wherein

X and $An^{(-)}$ have the indicated meaning, $R_4$ denotes an alkyl or aralkyl radical and $R_5$ and $R_6$ independently of one another denote hydrogen or an alkyl, cycloalkyl, aralkyl or aryl radical, and $R_5$ and $R_6$ can be cyclised with one another or with $B_1$ and $An^{(-)}$ denotes an anion and wherein the rings $A_1$ and $B_1$ and the substituents $R_4$, $R_5$ and $R_6$ can carry further non-ionic substituents.

Particularly preferred dyestuffs of the formula (I) are those of the formula

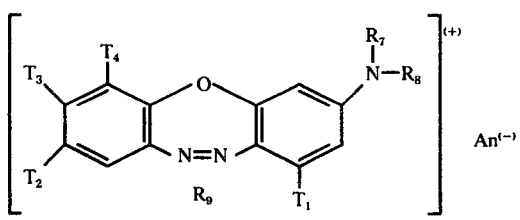

wherein
R₇ and R₈ independently of one another denote hydrogen, methyl, ethyl or propyl, which can be substituted by chlorine, bromine, nitrile, thiocyanate, hydroxyl, methoxy, ethoxy, chloroethoxy, bromoethoxy, cyanoethoxy, acetoxy, propionyloxy, butyryloxy, benzoyloxy, methoxycarbonyl, ethoxycarbonyl, phenoxycarbonyl, methoxycarbonyloxy, ethoxycarbonyloxy or phenoxycarbonyloxy, or denote cyclohexyl, benzyl or phenyl, it being possible for the phenyl radical to be substituted by methyl, ethyl, methoxy, ethoxy, phenyloxy, halogen, nitrile or nitro, R₉ denotes methyl, ethyl, propyl, butyl, aminocarbonylethyl or benzyl, T₁ and T₄ independently of one another denote hydrogen, chlorine, methyl, methoxy or ethoxy, T₂ and T₃ independently of one another denote hydrogen, fluorine, chlorine, bromine, methyl, ethyl, n-propyl, isopropyl, n-butyl, isobutyl, tert-butyl, isoamyl, cyclohexyl, β-chloroethyl, β-cyanoethyl, β-hydroxyethyl, β- or γ-hydroxypropyl, benzyl, phenyl, hydroxyl, methoxy, ethoxy, n-propoxy, isopropoxy, n-butoxy, βmethoxyethoxy, β-ethoxyethoxy, benzyloxy, 2-phenylethyloxy, phenylpropyl-(2,2)-oxy, phenoxy, methylthio, ethylthio, propylthio, benzylthio, phenylthio, formyl, acetyl, n-propionyl, n-butyryl, benzoyl, benzylcarbonyl, methoxycarbonyl, ethoxycarbonyl, acetylamino, ureido, N-methylureido, carbamoyl, N-methylcarbamoyl, N,N-dimethylcarbamoyl, sulphamoyl, N-methylsulphamoyl, N-ethylsulphamoyl, N,N-dimethylsulphamoyl, N,N-diethylsulphamoyl, methoxycarbonylmethyl, ethoxycarbonylmethyl, methylphenoxy, chlorophenoxy or methoxyphenoxy and An⁽⁻⁾ denotes an anion.

The new dyestuffs I can be manufactured by reaction of cyclic azo compounds of the formula

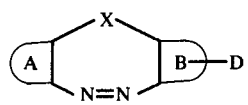

wherein
A, B, D and X have the indicated meaning with quaternising agents of the general formula R—An VIII wherein
R and An have the indicated meaning.

Suitable azo compounds of the formula (VII) can be manufactured analogously to methods described in the literature, for example dibenzotriazepine derivatives such as

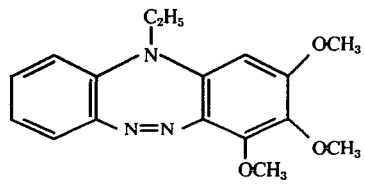

can be manufactured by ethylation, with ethyl chloride, of the sodium salt of

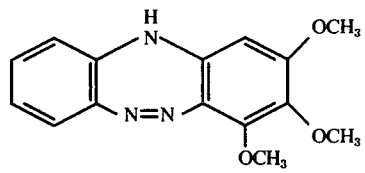

described by E. Kirchner and H. Bretschneider in Monatsh. Chem. 102, 162 (1971). Further heterocyclic compounds suitable as starting compounds, such as dibenzotriazepines, oxadiazepine derivatives and dibenzothiadiazepines are in part known or can be manufactured analogously following the instructions of N. L. Allinger and G. A. Youngdale, Tetrahedron Letters 9, 10 (1959) and J. Amer. Chem. Soc. 84, 1020, 1024 (1962), of J. J. Eatough, L. S. Fuller, R. H. Good and R. K. Smalley, J. Chem. Soc. (London) Sect. C 1874, and DAS (German Published Specification) 1,220,952, J. R. Geigy AG.

Thus, for example, a compound of the formula

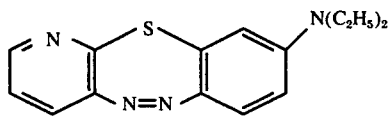

is obtained by reaction of 2-chloro-3-nitro-pyridine with 3-diethylaminothiophenol to give 2(3'-diethylaminothiophenoxy)-3-nitro-pyridine, reduction to the 3-amino compound, diazotisation and intramolecular coupling. The oxadiazepine derivative

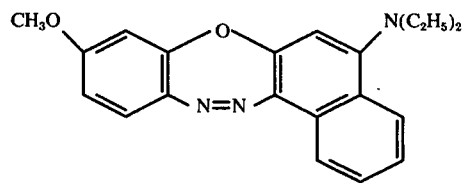

is obtained, for example, by reaction of 3-chloro-4-nitroanisole with 1-diethylamino-3-hydroxynaphthalene to give 1-diethylamino-3-(5'-methoxy-2'-nitrophenoxy)-naphthalene, reduction to the 2'-amino compound, diazotisation and internal coupling.

Analogously, for example, the following heterocyclic compounds are obtained:

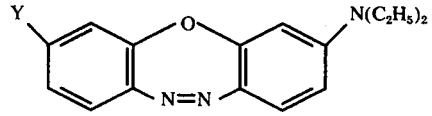

-continued

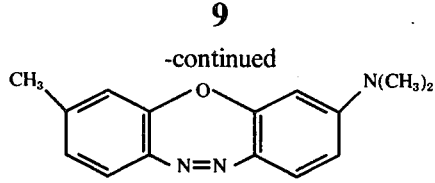

Y = H, Cl or C₆H₅—O

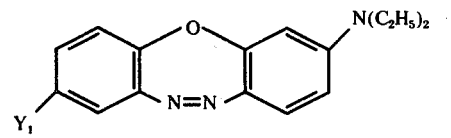

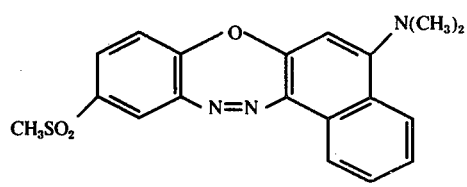

Y₁ = Cl, Br, NO₂, CH₃—CO, C₆H₅—CO or HO—CH₂

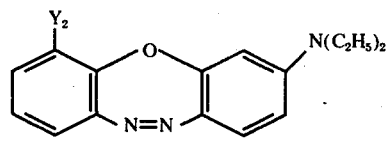

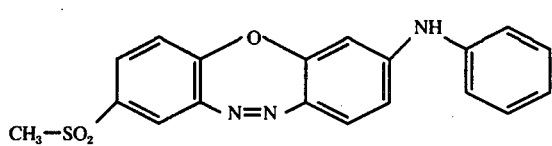

Y₂ = Cl or CH₃

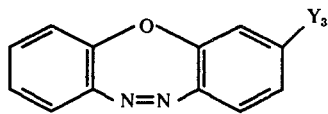

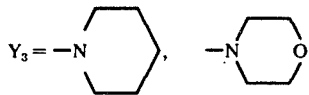

The quaternisation is carried out, for example, by warming solutions or suspensions of the non-quaternised compounds (VII), which have, if necessary, been freed of acid, in an inert medium with an alkylating agent to 0°–140° C, preferably to temperatures between room temperature and 80° C. For this, excess of the alkylating agent can also be used as the solvent.

Suitable inert solvents are inorganic liquids, for example hydrocarbons, chlorohydrocarbons or nitrohydrocarbons, such as benzine, ligroin, cyclohexane, tetralin, benzene, toluene, xylene, tetrachloroethane chloroform, methylene chloride, carbon tetrachloride, chlorobenzene, dichlorobenzene, nitrobenzene or nitromethane and, for example, also ketones, such as acetone or methyl ethyl ketone, and, for example, also acid amides or acid anhydrides, such as dimethylformamide, N-methylacetamide or acetic anhydride and, for example, also various ethers or esters, such as dioxane or ethyl acetate, but, for example, also other inert solvents such as dimethylsulphoxide or acetonitrile.

Suitable quaternising agents are, for example, dimethyl sulphate, diethyl sulphate, di-n-butyl sulphate, di-iso-amyl sulphate, dimethyl pyrosulphate, benzenesulphonic acid methyl ester, ethyl ester, n-propyl ester, iso-propyl ester and isobutyl ester, p-toluenesulphonic acid methyl ester, ethyl ester, n-propyl ester, iso-propyl ester and iso-butyl ester, chloromethane, bromomethane, iodomethane, chloroethane, bromoethane, iodoethane, 1-chloropropane, 1-bromopropane, 1-iodopropane, 2-chloropropane, 2-bromopropane, 2-iodopropane, 1-bromobutane, 1-chlorobutane, 1-iodobutane, 1-bromo-2-methylpropane, 1-chloro-2-methylpropane, 1-chloropentane, 1-bromopentane, 1-iodopentane, 1-chlorohexane, 1-bromohexane, 1-iodohexane, bromocyclohexane, 1-bromoheptane, 1-bromooctane, 1-iodooctane, 2-iodooctane, 1-bromodecane, 1-bromododecane, benzyl chloride, benzyl bromide, allyl chloride, allyl bromide, 2-bromo- and 2-chloro-diethyl ester and chloroacetic and bromoacetic acid esters, such as chloroacetic and bromoacetic acid ethyl ester, ethylene oxide, acrylic acid, acrylic acid methyl ester, acrylic acid amide and acrylonitrile.

The quaternisation can also be carried out in the presence of alkaline agents, especially in the presence of tertiary amines which possess bulky substituents at the N atom, in accordance with Belgian Pat. Specification No. 735,565. Tri-iso-propanolamine is particularly suitable as an amine with bulky substituents.

The new dyestuffs of the formula (I) and (III) to (VI) are valuable products which can be used for dyeing and printing textile and non-textile materials, for example materials of leather, tannin-treated cotton, cellulose, synthetic high molecular polyamides and high molecular polyurethanes, and for dyeing fibres containing lignin such as coir, jute and sisal. They are furthermore suitable for the manufacture of writing fluids, rubber stamp inks and ball point pen pastes and can also be used in flexographic printing.

Flocks, fibres, filaments, tapes, woven fabrics or knitted fabrics of polyacrylonitrile or asymmetrical dicyanoethylene, or of copolymers of acrylonitrile, containing a proportion of at least 85% of acrylonitrile, with other vinyl compounds, such as vinyl chloride, vinylidene chloride, vinyl fluoride, vinyl acetate, vinylpyridine, vinylimidazole, vinyl alcohol, or acrylic and methacrylic acid esters and amides are particularly suitable for dyeing with the basic dyestuffs of the general formula (I) and (III) to (VI). Equally, it is possible to dye flocks, fibres, filaments, tapes, woven fabrics or knitted fabrics of acid-modified synthetic materials, especially of acid-modified aromatic polyesters as well as acid-modified polyamide fibres. Acid-modified aromatic polyesters are, for example, polycondensation products of sulphoterephthalic acid and ethylene glycol, that is to say polyethylene glycol terephthalates containing sulphonic acid groups (type DACRON 64 of E.I. DuPont de Nemours and Company), such as are described in Belgian Pat. Specification No. 549,179 and U.S.A. Pat. Specification No. 2,893,816.

Dyeing can be carried out from weakly acid liquors in which case the material is appropriately introduced into the dye bath at 40° to 60° C and then dyed at the boil. It is also possible to dye under pressure at temperatures above 100° C. Furthermore, the dyestuffs can be added to spinning solutions for the manufacture of fibres containing polyacrylonitrile or be applied to the unstretched fibre.

The dyeings of the dyestuffs according to the invention, of the formulae (I) and (III) to (VI), on materials of polyacrylonitrile or acid-modified polyester fibres, are distinguished by very good fastness to light, wet processing, rubbing and sublimation and by a high affinity to the fibre. With anionic precipitants such as alumina, tannin, phosphotungstic or phosphomolybdic acids the dyestuffs form light-fast pigments which can advantageously be employed in paper printing.

The dyestuffs can be employed individually or as mixtures. They are very suitable for dyeing shaped articles of polymers or copolymers of acrylonitrile or asymmetrical dicyanoethylene, acid-modified aromatic polyesters or acid-modified synthetic polyamides in chlorinated hydrocarbons as the dye bath, if they carry substituents which assist solubility in chlorohydrocarbons, such as, for example, the tert.-butyl group, or if the anion $An^{(-)}$ in the formulae (I) and (III) to (VI) is the anion of a monobasic organic acid with 4 – 30 carbon atoms.

Examples of such organic acids are: 2-ethylcaproic acid, lauric acid, oleic acid, linoleic acid, a mixture of aliphatic carboxylic acids with 15 – 19 C atoms (Versatic Acid 1519), a mixture of aliphatic carboxylic acids with 9 – 11 C atoms (Versatic Acid 911), coconut fatty acid first runnings, tetradecanoic acid, undecylenic acid, dimethylpropanoic acid, dimethylacetic acid, carboxylic acids of which the carbon chain is interrupted by hetero-atoms, such as nonylphenoltetraethylene glycol-ether-propionic acid, nonylphenoldiethylene glycol-ether-propionic acid, dodecyl-tetraethylene glycol-ether-propionic acid, 3-(nonyloxy)-propionic acid, 3-(isotridecyloxy)-propionic acid, 3-(isotridecyloxy)-diethylene glycol-ether-propionic acid, the ether-propionic acid of an alcohol mixture with 6 – 10 C atoms, nonylphenoxyacetic acid, aromatic carboxylic acids, such as tert.-butylbenzoic acid, cycloaliphatic carboxylic acids, such as hexahydrobenzoic acid, cyclohexenecarboxylic acid, abietic acid and sulphonic acids, such as tetrapropylenebenzenesulphonic acid.

Dyestuffs of the formulae (I) and (III) to (VI), in which the anion $An^{(-)}$ is the anion of one of these acids listed here, are particularly preferred.

If the dyestuffs according to the invention are in the form of salts of the said monobasic organic acids with 4 – 30 C atoms, concentrated solutions, of good stability, of these dyestuffs in chlorohydrocarbons can be manufactured, optionally with the addition of polar organic solvents which are completely miscible with chlorohydrocarbons, such as butyrolactone, dimethylformamide, methanol, dioxane, acetonitrile, methyl ethyl ketone, nitrobenzene, dimethylsulphoxide, benzonitrile and 2-nitrochlorobenzene.

To manufacture such solutions, the dyestuffs according to the invention, in the form of the free bases or as salts of organic acids with 4 – 30 C atoms, are stirred with chlorohydrocarbons and monobasic organic acids with 4 – 30 C atoms, optionally with the addition of polar organic solvents which are completely miscible with chlorohydrocarbons, and if necessary at an elevated temperature.

EXAMPLE 1

3.0 g of sodium carbonate and 47.5 ml of purified dimethyl sulphate are added to a solution of 29.7 g of 2-diethylamino-9-methoxy-dibenzo-1,4,5-oxadiazepine in 200 ml of water and the mixture is warmed to 50° C whilst stirring. On reaching 50° C, the reaction is almost complete. The mixture is stirred for a further 30 minutes at this temperature. 650 ccs of water are added to the solution thus obtained and the mixture is stirred overnight to decompose excess dimethyl sulphate. After adding 95 ccs of fluoboric acid, the mixture is stirred for a further hour and the dyestuff which has precipitated is filtered off and dried.

The dyestuff thus obtained, of the formula

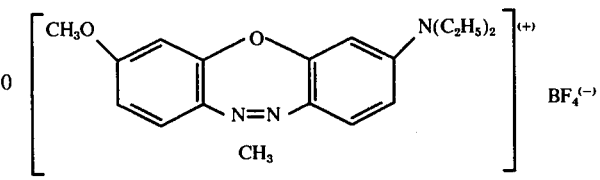

dyes polyacrylonitrile materials in clear violet shades. The dyeings have very good fastness to light and to decatising.

If, in Example 1, 2-diethylamino-9-methoxydibenzo-1,4,5-oxadiazepine is replaced by appropriately substituted dibenzo-1,4,5-oxadiazepines and the dyestuff cations produced in the reaction are precipitated with the anions indicated, the dyestuffs of the formula

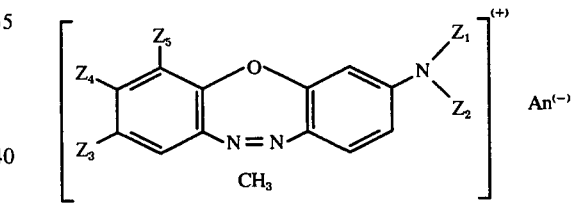

are obtained.

| $Z_1 = Z_2$ | $Z_3$ | $Z_4$ | $Z_5$ | An | Colour shade on polyacrylonitrile |
|---|---|---|---|---|---|
| $CH_3$ | H | H | H | $ZnCl_3$ | red |
| $CH_3$ | Cl | H | H | $ZnCl_3$ | red |
| $CH_3$ | H | $OCH_3$ | H | $ZnCl_3$ | violet |
| $C_2H_5$ | H | H | H | $BF_4$ | red |
| $C_2H_5$ | H | H | Cl | $BF_4$ | red |
| $C_2H_5$ | H | H | $CH_3$ | $BF_4$ | red |
| $C_2H_5$ | $CH_3$ | H | H | $ZnCl_3$ | red |
| $C_2H_5$ | Cl | H | H | $ZnCl_3$ | red |
| $C_2H_5$ | $OCH_3$ | H | H | $ZnCl_3$ | red |
| $C_6H_5CH_2$ | H | Br | H | $ZnCl_3$ | violet |
| $C_2H_5$ | Br | H | H | $ZnCl_3$ | red |
| $C_2H_5$ | $CF_3$ | H | H | $BF_4$ | red |
| $C_3H_7$ | $C_2H_5-SO_2$ | H | H | $ZnCl_3$ | red |

EXAMPLE 2

5.0 g of sodium carbonate and 23.7 ccs of freshly distilled dimethyl sulphate are added to a solution of 16.1 g of 2-(ethyl-hexylamino)dibenzo-1,4,5-oxadiazepine in 140 ml of acetone and the mixture is kept at 40° C for 20 minutes, whilst stirring. In the course thereof, complete reaction occurs. The product is filtered off and the sodium carbonate residue is rinsed with 50 ml of acetone. The acetone is stripped off the combined acetone solutions, 100 ccs of water are added to the residue and after filtering off undissolved material zinc chloride and sodium chloride are added to precipitate the dyestuff salt. The dyestuff salt of the formula

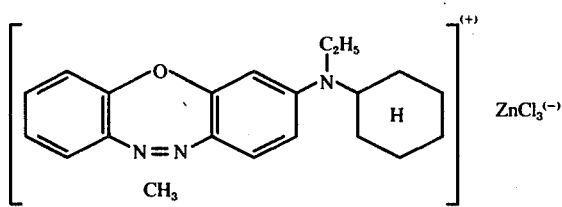

is filtered off and dried and is obtained as a readily water-soluble dyestuff which dyes polyacrylonitrile materials in clear red shades. The dyeings possess good fastness to decatising and very good fastness to light.

If, in Example 2,2-(ethyl-hexylamino)dibenzo-1,4,5-oxadiazepine is replaced by suitably substituted dibenzo-1,4,5-oxadiazepines, the following dyestuffs are obtained.

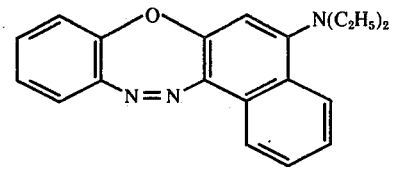

| $Z_1$ | $Z_2$ | $Z_3$ | $Z_4$ | An | Colour shade on polyacrylonitrile |
|---|---|---|---|---|---|
| $CH_3$ | $C_4H_9$ | Cl | H | $BF_4$ | red |
| $CH_3$ | $C_2H_4-Cl$ | H | $OCH_3$ | $ZnCl_3$ | violet |
| $C_2H_5$ | $C_2H_4-Cl$ | H | H | $BF_4$ | red |
| $C_2H_5$ | H | H | H | $BF_4$ | red |
| $CH_3$ | $C_2H_4-OH$ | H | H | $ZnCl_3$ | red |
| $CH_3$ | $C_2H_4-OCH_3$ | H | H | $BF_4$ | red |
| $C_4H_9$ | $C_2H_4-O-CH_3$ | H | H | $BF_4$ | red |
| $C_2H_5$ | $C_2H_4-O_2CCH_3$ | H | H | $BF_4$ | red |
| $C_2H_5$ | $C_2H_4-CN$ | H | H | $BF_4$ | red |

| $R_4$ | $R_5$ | $Z_3$ | $Z_4$ | An | Colour shade on polyacrylonitrile |
|---|---|---|---|---|---|
| $C_2H_5$ | $C_2H_4-O-C_6H_5$ | H | H | $CH_3SO_4$ | red |
| $CH_3$ | $C_2H_4-C_6H_5$ | H | H | $ZnCl_3$ | red |
| $CH_3$ | $C_2H_4-CO_2-C_2H_5$ | H | H | $BF_4$ | red |

If, in Example 2, the 23.7 ccs of dimethyl sulphate are replaced by 30 ccs of diethyl sulphate and the mixture is kept for 40 minutes at 40° C, whilst stirring, the dyestuff of the formula

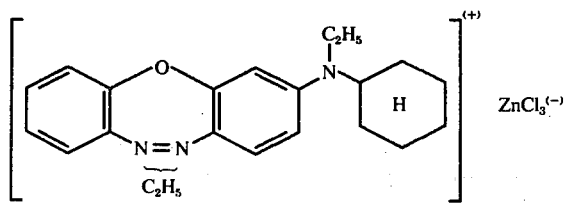

is obtained, which dyes polyacrylonitrile materials in clear red shades.

EXAMPLE 3

6.35 g of the cyclic azo compound of the formula

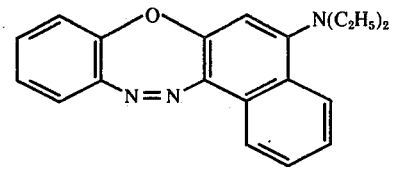

6.0 g of sodium carbonate and 12.6 g of dimethyl sulphate in 50 ml of acetonitrile are warmed to 64° C whilst stirring and kept at this temperature for 30 minutes. The product is filtered off and rinsed with 20 ml of acetonitrile. The filtrate and the wash solution are combined and the solvent is stripped off in a waterpump vacuum. The residue is taken up in 40 ml of water, 0.5 cc of concentrated hydrochloric acid is added and the dyestuff salt is precipitated by adding 20 ccs of fluoboric acid. The product is filtered off and dried and a water-soluble dyestuff is obtained, which dyes polyacrylonitrile materials in a violet colour having good fastness properties.

EXAMPLE 4

14.4 g of the cyclic azo compound of the formula

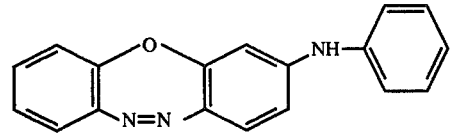

are stirred with 100 ml of acetonitrile and 3 g of sodium carbonate and 5 ml of dimethyl sulphate are added. The mixture is stirred for 30 minutes at 30° C. 100 ml of water are added and the mixture is stirred to decompose the excess dimethyl sulphate. The dyestuff solution is then concentrated in vacuo. The dyestuff is precipitated from the concentrated aqueous solution by adding fluoboric acid and is filtered off and dried. The dyestuff salt is water-soluble and dyes polyacrylonitrile materials in violet shades.

If in Example 4, instead of 2-anilino-dibenz-1,4,5-oxadiazepine, the dibenzoxadiazepines of the formulae

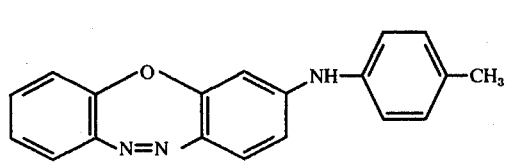

and

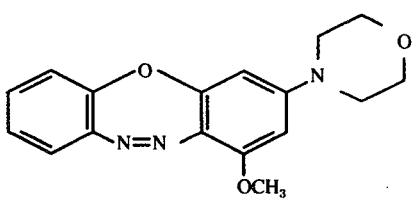

are used as starting materials, the corresponding violet cationic dyestuffs which are alkylated at the azo bridge are obtained. If the dibenzoxadiazepines of the formulae

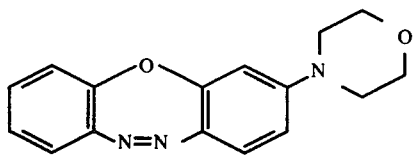

and

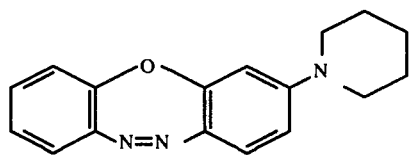

are used, the corresponding red dyestuff salts are obtained, of which the weakly acid aqueous solutions dye polyacrylonitrile materials in fast red shades.

EXAMPLE 5

13.4 g of 2-diethylamino-dibenz-1,4,5-oxadiazepine are stirred with 5 ml of hydrochloric acid and 17 ml of glacial acetic acid. 35 g of acrylamide are added and the mixture is warmed to 90° C for 1 hour. After cooling the reaction solution, 120 ml of a solution of zinc chloride containing hydrochloric acid are added and the mixture is carefully neutralised with ammonia. After stirring for five hours, the dyestuff salt which has precipitated is filtered off and dried. The dyestuff thus obtained, of the formula

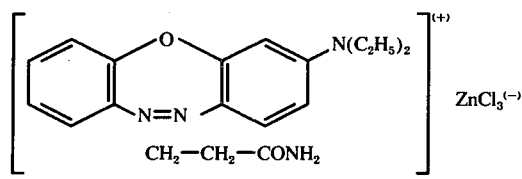

dyes polyacrylonitrile materials in clear red shades.

EXAMPLE 6

Ethylene oxide is passed in a slow stream into a 10% strength solution of the compound of the formula

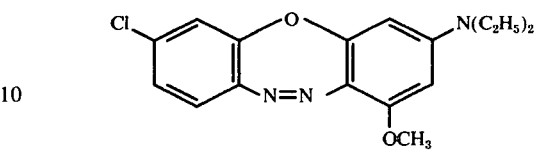

in glacial acetic acid at 60° C for several hours, until it is possible to demonstrate, by thin layer chromatography, complete conversion to a violet basic dyestuff. The mixture is then diluted to 10 times its volume with water and the dyestuff is precipitated as the chlorozincate by means of sodium chloride solution and zinc chloride solution. The resulting dyestuff dyes polyacrylonitrile materials in a violet colour having very good fastness properties.

If in Example 6 propylene oxide, epichlorohydrin, glycidamide, glycidyl ethyl ether or glycidyl alcohol are employed instead of ethylene oxide, under otherwise identical conditions, similar violet dyestuffs are obtained.

EXAMPLE 7

A polyacrylonitrile fabric is printed with a printing paste which has been manufactured in the following manner: 30 parts by weight of the dyestuff of the probable formula

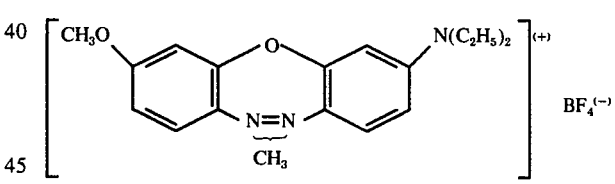

50 parts by weight of thiodiethylene glycol, 30 parts by weight of cyclohexanol and 30 parts by weight of 30% strength acetic acid are covered wth 330 parts by weight of hot water and the resulting solution is added to 500 parts by weight of crystal gum (gum arabic as thickener). Finally, 30 parts by weight of zinc nitrate solution are also added. The resulting print is dried, steamed for 30 minutes and subsequently rinsed. A violet print of very good fastness properties is obtained.

EXAMPLE 8

Acid-modified polyglycol terephthalate fibres are introduced, using a liquor ratio of 1:40, into an aqueous bath at 20° C which contains, per litre, 3 to 10 g of sodium sulphate, 0.1 – 1 g of oleyl polyglycol ether (50 mols of ethylene oxide), 0 – 15 g of dimethylbenzyl dodecyclammonium chloride and 0.15 g of the dyestuff of the formula

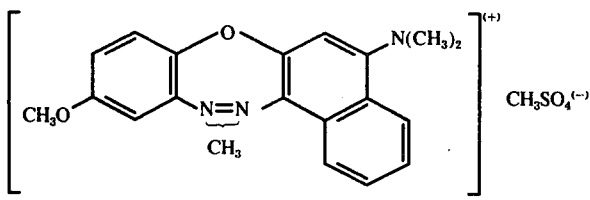

and which has adjusted to pH 4 – 5 with acetic acid. The bath is heated to 100° C over the course of 30 minutes and kept at this temperature for 60 minutes. Thereafter the fibres are rinsed and dried. A violet dyeing having very good fastness properties is obtained.

EXAMPLE 9

Polyacrylonitrile fibres are introduced, using a liquor ratio of 1:40, into an aqueous bath at 40° C, which contains, per litre, 0.75 g of 30% strength acetic acid, 0.38 g of sodium acetate and 0.15 g of the dyestuff of the formula

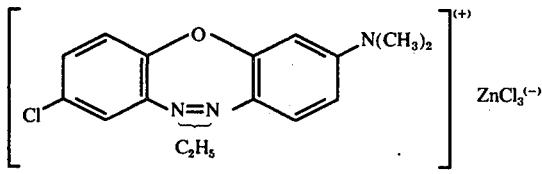

The bath is heated to the boil over the course of 20 – 30 minutes and kept at this temperature for 30 – 60 minutes. After rinsing and drying, a red dyeing having very good fastness properties is obtained.

EXAMPLE 10

In a dyeing beaker of 500 ml capacity located in a heated water bath, 0.055 g of the dyestuff of the probable formula

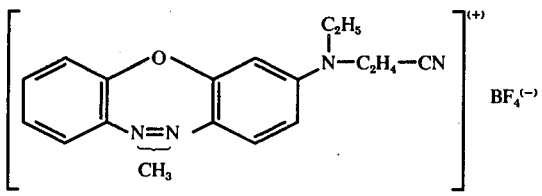

are worked into a paste with a 20-fold amount of hot water, with the addition of a little acetic acid, and the paste is dissolved with hot water. Further, 0.5 g of the reaction product of 50 mols of ethylene oxide with 1 mol of oleyl alcohol is added to the dyeing liquor, which is made up to 500 ml with cold water. The pH value of the dyeing liquor is adjusted to 4.5 – 5 with acetic acid or sodium acetate.

10 g of piece goods of acid-modified polyamide are constantly agitated in this dyeing liquor whilst raising the temperature to 100° C over the course of 15 minutes. Dyeing is carried out at the boil for 15 – 20 minutes and the material is rinsed with cold water and subsequently dried, for example by ironing or in a drying cabinet at 60° – 70° C. A material dyed red is obtained.

EXAMPLE 11

Polyacrylonitrile fibres were introduced, using a liquor ratio of 1:10, into a perchloroethylene bath which contains, per liter, 1 g of oleic acid ethanolamide, 1 g of the reaction product of 1 mol of oleyl alcohol with 20 mols of ethylene oxide, 8 g of water and 1 g of glacial acetic acid as well as 1 g of the dyestuff of the probable formula

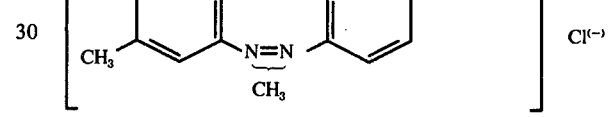

The dyebath is heated to 100° over the course of 60 minutes, with the dyeing apparatus closed and whilst vigorously agitating the liquor. Thereafter the fibres are rinsed and dried. A red dyeing having very good fastness properties is obtained.

EXAMPLE 12

25 parts of the dyestuff from Example 11 are suspended in 150 parts of perchloroethylene and 65 parts of butyrolactone are added, followed by 15 parts by weight of 2-ethylcaproic acid. The dyestuff dissolves to give a red colour shade. The solution is stirred for a further hour at 50° C and is filtered after having again cooled it to room temperature. A stable solution is obtained, which is outstandingly suitable for dyeing polyacrylonitrile materials from chlorohydrocarbon solutions.

EXAMPLE 13

50 parts of fibre yarn of anionically modified polyacrylonitrile are introduced at 22° C, into a dye bath which consists of a mixture of 4 parts of the perchloroethylene dyestuff solution described in Example 11, 4 parts of oleic acid ethanolamide, 4 parts of the reaction product of 1 mol of oleyl alcohol with 20 mols of ethylene oxide, 1 part of glacial acetic acid and 8 parts of water in 983 parts of perchloroethylene. The bath is brought to 100° C over the course of 30 minutes whilst vigorously circulating the liquor and is kept at this temperature for 1 hour. After this time, the liquor is separated off and the yarn is freed of adhering solvent in a stream of air. A red dyeing is obtained.

We claim:
1. Cationic dyestuff of the formula

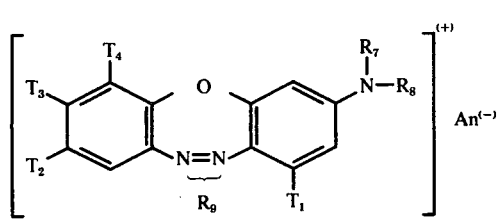

wherein
- R_7 and R_8 independently of one another are hydrogen; methyl; ethyl; propyl; methyl, ethyl or propyl substituted by chlorine, bromine, nitrile, thiocyanate, hydroxyl, methoxy, ethoxy, chloroethoxy, bromoethoxy, cyanoethoxy, acetoxy, propionyloxy, butyryloxy, benzoyloxy, methoxycarbonyl, ethoxycarbonyl, phenoxycarbonyl, methoxycarbonyloxy, ethoxycarbonyloxy, or phenoxycarbonyloxy; cyclohexyl; benzyl; phenyl; or phenyl substituted by methyl, ethyl methoxy, ethoxy, phenyloxy, halogen, nitrile or nitro;
- R_9 is methyl, ethyl, propyl, butyl, aminocarbonylethyl or benzyl;
- T_1 and T_4 independently of one another are hydrogen, chlorine, methyl, methoxy or ethoxy;
- T_2 and T_3 independently of one another are hydrogen, fluorine, chlorine, bromine, methyl, ethyl, n-propyl, isopropyl, n-butyl, isobutyl, tert-butyl, isoamyl, cyclohexyl, β-chloroethyl, β-cyanoethyl, β-hydroxyethyl, β- or γ-hydroxypropyl, benzyl, phenyl, hydroxyl, methoxy, ethoxy, n-propoxy, isopropoxy, n-butoxy, β-methoxyethoxy, β-ethoxyethoxy, benzyloxy, 2-phenylethyloxy, phenylpropyl-(2,2)-oxy, phenoxy, methylthio, ethylthio, propylthio, benzylthio, phenylthio, formyl, acetyl, n-propionyl, n-butyryl, benzoyl, benzylcarbonyl, methoxycarbonyl, ethoxycarbonyl, acetylamino, ureido, N-methylureido, carbamoyl, N-methylcarbamoyl, N,N-dimethylcarbamoyl, sulphamoyl, N-methylsulphamoyl, N-ethylsulphamoyl, N,N-dimethylsulphamoyl, N,N-diethylsulphamoyl, methoxycarbonylmethyl, ethoxycarbonylmethyl, methylphenoxy, chlorophenoxy or methoxyphenoxy; and
- $An^{(-)}$ is an anion.

2. Cationic dyestuff according to claim 1 of the formula

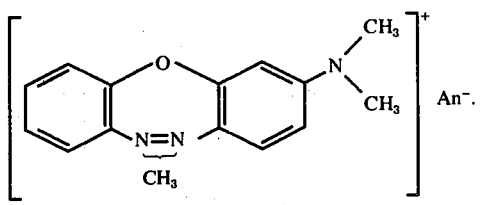

3. Cationic dyestuff according to claim 1 of the formula

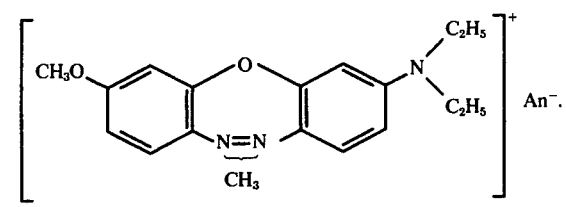

4. Cationic dyestuff according to claim 1 of the formula

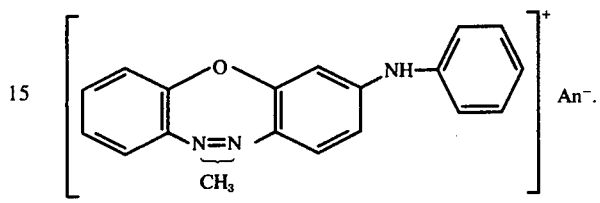

5. Cationic dyestuff of the formula

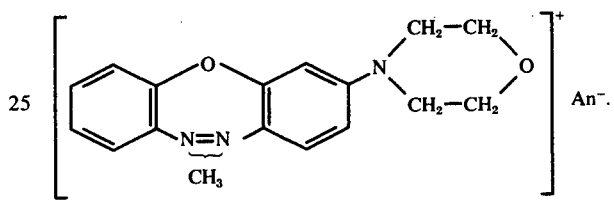

6. Cationic dyestuff of the formula

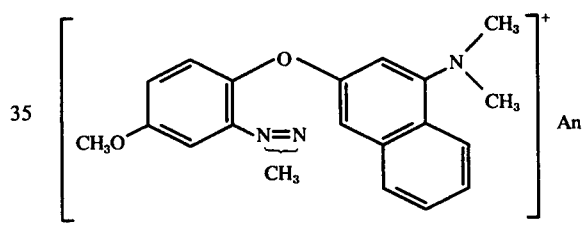

7. Cationic dyestuff of claim 1 selected from the group consisting of

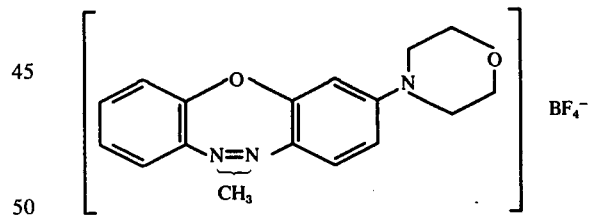

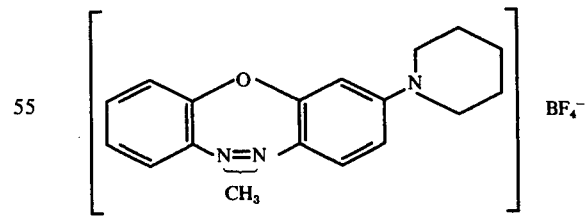

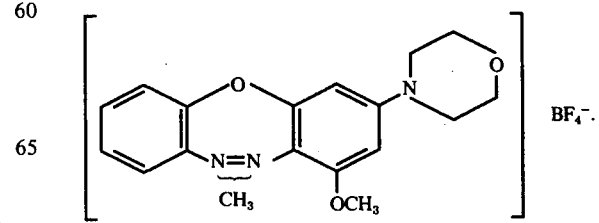

* * * * *